United States Patent [19]

Dage et al.

[11] Patent Number: 5,002,961

[45] Date of Patent: Mar. 26, 1991

[54] METHOD FOR REDUCING INJURY WITH IMIDAZOL-2-THIONECARBOXAMIDES

[75] Inventors: Richard C. Dage; Richard A. Schnettler, both of Cincinnati, Ohio

[73] Assignee: Merrell Dow Pharmaceuticals, Cincinnati, Ohio

[21] Appl. No.: 545,684

[22] Filed: Jun. 28, 1990

Related U.S. Application Data

[63] Continuation of Ser. No. 473,146, Jan. 31, 1990, abandoned, which is a continuation of Ser. No. 379,729, Jul. 14, 1989, abandoned, which is a continuation of Ser. No. 310,516, Feb. 14, 1989, abandoned, which is a continuation of Ser. No. 110,143, Oct. 19, 1987, abandoned.

[51] Int. Cl.$^5$ .................. A61K 31/44; A61K 31/415
[52] U.S. Cl. ..................................... 514/392; 514/341
[58] Field of Search ............................. 514/392, 341

[56] References Cited

FOREIGN PATENT DOCUMENTS 2110668  6/1983  United Kingdom .

OTHER PUBLICATIONS

R. C. Smith, et al., Biochemical Pharmacology; 36(9), 1457–1460 (1987).

J. M. McCord, New England J. Med. 312(3); 159–163 (1915).

*Primary Examiner*—Allen J. Robinson
*Attorney, Agent, or Firm*—Michael J. Sayles

[57] ABSTRACT

Certain 2-oxo- and 2-thioxoimidazol-4-carboxamides are reported to reduce reperfusion injury which is the injury which occurs when molecular oxygen is reintroduced into an ischemic tissue. These compounds could be used to prevent much of the damage which occurs to the heart of a heart attack victim.

16 Claims, No Drawings

METHOD FOR REDUCING INJURY WITH IMIDAZOL-2-THIONECARBOXAMIDES

This is a continuation of application Ser. No. 473,146, filed Jan. 31, 1990, now abandoned, which is a continuation of application Ser. No. 379,729 filed July 14, 1989, now abandoned, which is a continuation of application Ser. No. 310,516 filed Feb. 14, 1989, now abandoned, which is a continuation of application Ser. No. 110,143, filed Oct. 19, 1987, now abandoned.

FIELD OF THE INVENTION

This invention relates to the use of certain pharmaceutical agents to reduce damage caused during reperfusion of ischemic tissue.

BACKGROUND OF THE INVENTION

Heart attack is a leading cause of death and results most commonly from an imparment of the blood supply to the heart muscle (myocardium). Oxygen deprivation to the heart muscle, cardiac ischemia, results in impaired function and eventually myocardial cell death and necrosis (infarction). Survival of myocardial infarction victims depends on the extent or size of the infarcted area which has a femoral component. Transformation of cells in the ischemic area from reversibly to irreversibly injured occurs over the course of several hours. Without reperfusion infarct extension continues for up to six hours after the start of an ischemic event. Establishment of reperfusion of the ischemic area stops an evolving myocardial infarction and salvages tissue. However, recent findings suggest that reperfusion of the ischemic tissue with oxygenated blood results in injury caused by oxygen derived free radicals.

2-Oxo- and 2-thioxo-imidazolecarboxamides are known from British Patent number 2,110,668 to possess antiallergy activity. More recently, the antioxidant properties of 2,3-dihydro-5-methyl-2-oxo- and 2-thioxo-1H-imidazole-4-carboxamide and 2,3-dihydro-N,N,5,-trimethyl-2-oxo- and 2-thioxo-1H-imidazole-4-carboxamide were reported by R. C. Smith, et al., Biochemical Pharmacology, 36(9), 1457–1460 (1987). Now it has been discovered that the 2-thioxoimidazolecarboxamides when administered to a patient prior to an ischemic event, during an ischemic event, or during the period of time subsequent to an ischemic event during which reperfusion damage occurs, prevent or lessen the damage which normally occurs when circulation is restored to the portion of the heart formerly deprived of blood.

SUMMARY OF THE INVENTION

The imidazol-2-thionecarboxamides having formula 1:

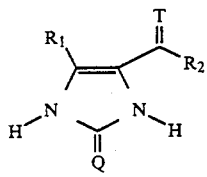

Formula 1 wherein Q and T each independently are a divalent oxygen or sulfur group;
$R_1$ is a hydrogen or a ($C_1$-$C_4$)alkyl group; and
$R_2$ is a —$NH_2$, —$NH(R_3)$, or —$N(R_3)(R_4)$ group wherein $R_3$ is a ($C_1$-$C_4$)alkyl, 2-, 3-, or 4-pyridinyl, 2- or 3-furanyl, 2- or 3-thienyl, 2- or 3-pyranyl, or a phenyl group optionally substituted at the ortho, meta, or para position with a ($C_1$-$C_4$)alkyl, ($C_1$-$C_4$)alkoxy, ($C_1$-$C_4$)alkylthio, ($C_1$-$C_4$)alkylsulfone, ($C_1$-$C_4$)alkylsulfoxide, hydroxy, halo, trifluoromethyl, cyano, carboxy, carb($C_1$-$C_4$)alkoxy, ($C_1$-$C_4$)alkanoylamino, imidazolyl, or methylenedioxy group and wherein $R_4$ is ($C_1$-$C_4$)alkyl group; as well as their pharmaceutically acceptable salts are useful in preventing or lessening reperfusion injury, i.e. the injury resulting from the reintroduction of molecular oxygen to an ischemic tissue.

DETAILED DESCRIPTION OF THE INVENTION

As used herein the term ($C_1$-$C_4$)alkyl and the ($C_1$-$C_4$)alkyl portion of the alkoxy, alkylthio, alkylsulfoxide, alkylsulfone, carbalkoxy, or alkanoylamino groups means straight and branched chain alkyl groups having from one to four carbon atoms and includes methyl, ethyl, n-propyl, isopropyl, n-butyl, isobutyl, sec-butyl, and tert-butyl groups. The term "halo" group means a fluoro, chloro, bromo, or iodo group. A methylenedioxy group has the structure —$OCH_2$—.

The compounds of structure 1 are acidic and can form pharmaceutically acceptable salts with suitable inorganic or organic bases. These salts include those of the alkali metals such as lithium, sodium, or potassium. These salts can be prepared using conventional means such as by neutralizing a solution of the free acid in a polar solvent with a stoichiometric quantity of base, for example, an alkoxide such as sodium methoxide or potassium ethoxide or a hydride such as lithium hydride. These reactions are preferably carried out in solution. Suitable solvents are, for example, lower alcohols such as methanol, ethanol, isopropanol, or n-propanol; the ketonic solvents such as acetone or methyl ketone; or dimethylformamide (DMF). Typically about 1 molar equivalent of the free acid compound of structure 1 is allowed to react with about 1 molar equivalent of the base for about 1 minute to about 24 hours, preferably about 1 hour, depending on the reactants and the temperature which can be from about −30° C. to about 78° C., preferably about 0° C. to about 25° C. The compounds of structure 1 wherein $R_2$ is an optionally substituted pyridyl can form pharmaceutically acceptable salts with non-toxic organic or inorganic acids. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. Such salts can exist in either a hydrated or a substantially anhydrous form. The acid salts are prepared by standard techniques such as by dissolving the free base compound of structure 1 wherein $R_2$ is an optionally substituted pyridyl group in aqueous or aqueous-alcohol solvent or other suitable solvent containing the appropriate acid and isolating by evaporating the solution, or by reacting the free base in an organic solvent in which case the salt separates directly or can be obtained by concentration of the solution. In general the pharmaceutically acceptable salts are crystalline materials which are more soluble in water and various hydrophilic solvents and which in comparison to the free acid or base form generally demostrate higher melting points and an increased chemical stability. The preferred compounds of this invention are those compounds of structure 1 wherein Q is a divalent sulfur group and T is a divalent oxygen group. More preferred are those compounds of structure 1 wherein $R_1$ is a hydrogen or a methyl group. Also preferred are those compounds of formula 1 wherein $R_2$ is a —$NH_2$ group as well as those compounds wherein $R_2$ is a —$NH(R_3)$ group wherein $R_3$ is a lower alkyl or optionally substituted phenyl group. Also more preferred are those compounds of formula 1 wherein $R_2$ is a —$N(R_3)(R_4)$ group wherein $R_3$ and $R_4$ are both lower alkyl groups. Even more preferred are those compounds wherein $R_2$ is a —$N(R_3)(R_4)$ group wherein $R_3$ and $R_4$ are both methyl groups. The most preferred compound of this invention is that compound of formula 1 wherein T is an oxygen, $R_1$ is a methyl group, $R_2$ is a —$N(R_3)(R_4)$ group wherein $R_3$ and $R_4$ are each a methyl group, that is the compound 2,3-dihydro—N,N,5-trimethyl-2-thioxo-1H-imidazole-4-carboxamide.

Representative compounds of this invention include:
2,3-dihydro-5-methyl-2-thioxo-1H-imidazole-4-carboxamide;
2,3-dihydro-5-methyl-2-oxo-1H-imidazole-4-carboxamide;
2,3-dihydro-5-ethyl-N-(2-pyrridyl)-2-thioxo-1H-imidazole-4-carboxamide;
3-dihydro-5 ethyl-N-(2-pyrridyl)-2-oxo-1H-imidazole-4-carboxamide;
2,3-dihydro-5-methyl-N-(4-fluorophenyl)-2-thioxo-1H-imidazole-4-thiocarboxamide;
2,3-dihydro-5-methyl-N-(4-fluorophenyl)-2-oxo-1H-imidazole-4-thiocarboxamide;
2,3-dihydro-5-propyl-N-(3-trifluoromethylphenyl)-2-thioxo-1H-imidazole-4-carboxamide;
2,3-dihydro-5-propyl-N-(3-trifluoromethylphenyl)-2-oxo-1H-imidazole-4-carboxamide;
2,3-dihydro-N-(3-pyridyl)-2 thioxo-1H-imidazole-4-carboxamide;
2,3-dihydro-N-(3-pyridyl)-2-oxo-1H-imidazole-4-carboxamide;
2,3-dihydro-5-isobutyl-N-(2-methylphenyl)-2-thioxo-1H-imidazole-4-carboxamide;
2,3-dihydro-5-isobutyl-N-(2-methylphenyl)-2-oxo-1H-imidazole-4-carboxamide;
2,3-dihydro-N-methyl-N-(4-pyridyl)-2-thioxo-1H-imidazole-4-carboxamide;
2,3-dihydro-N-methyl-N-(4-pyridyl)-2-oxc-1H-imidazole-4-carboxamide;
2,3-dihydro-5-(n-butyl-N-ethyl-N-(3-methoxyphenyl)-2-thioxo-1H-imidazole-4-carboxamide;
2,3-dihydro-5-(n-butyl-N-ethyl-N-(3-methoxyphenyl)-2-oxo-1H-imidazole-4-carboxamide;
2,3-dihydro-N-methyl-N-(4-methythiophenyl)-2-thioxo-1H-imidazole-4-carboxamide;
2,3-dihydro-N-methyl-N-(4-methythiophenyl)-2-oxo-1H-imidazole-4-carboxamide;
2,3-dihydro-5-ethyl-N-methyl-N-(2-chlorophenyl)-2-thioxo-1H-imidazole-4-carboxamide;
2,3-dihydro-5-ethyl-N-methyl-N-(2-chlorophenyl)-2-oxo-1H-imidazole-4-carboxamide;
2,3-dihydro—N,5-dimethyl-2-thioxo-1H-imidazole-4-thiocarboxamide; and
2,3-dihydro—N,5-dimethyl-2-oxo-1H-imidazole-4-thiocarboxamide.

In general, the compounds of this invention are prepared by standard techniques known in the art. More specifically, the imidazolecarboxamides of this invention wherein T is an oxygen atom may be prepared by reaction of an aminoketoamide of formula 2

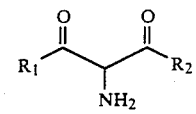

Formula 2 wherein $R_1$ and $R_2$ are as defined as in formula 1 with a cyanate or thiocyanate salt as appropriate, preferably a sodium or potassium cyanate or thiocyanate. This reaction is performed by mixing about 1 molar equivalent of the appropriate aminoketoamide with about 1 to about 5 molar equivalents, preferably about 1 molar equivalent, of a cyanate or thiocyanate in suitable solvent. The reaction is allowed to proceed for about 5 minutes to about 1 hour depending on the reactants, the solvent and the temperature which can be from about −10° to about 50° C., preferably 0° C. Suitable solvents for this reaction are any non-reactive solvents, preferably a water miscible solvent, for example, an organic acid such as acetic acid; an alcohol such as methanol or ethanol; or an ether such as tetrahydrofuran or p-dioxan. Preferably the solvent is mixed with water. The preferred solvent is aqueous ethanol.

The product of this reaction may be isolated by any art-known procedure such as by conversion to the corresponding sodium or potassium salt and reprecipitation with carbon dioxide or a mineral acid such as dilute hydrochloric acid.

When it is desired that T be a divalent sulfur atom, the corresponding imidazolecarboxamide of formula 1 wherein T is an oxygen atom is reacted with phosphorus pentasulfide, $P_2S_5$, by procedures generally known in the art. This reaction may be performed by mixing about 1 molar equivalent of the imidazolecarboxamide with about 1 to about 5 molar equivalents, preferably about 1 molar equivalent, of $P_2S_5$, together with a suitable solvent. This reaction is allowed to proceed for about 1 to about 10 hours, preferably about 5 hours, depending on the reactant, the solvent and the temperature which can be from about 25° C. to about 125° C., preferably about 80° C. A suitable solvent for this reaction is any non-reactive solvent, for example, a petroleum ether; a chlorinated hydrocarbon such as chloroform, methylene chloride, carbon tetrachloride or ethylene chloride; an ethereal solvent such as diethyl ether, tetrahydrofuran or p-dioxan; or an aromatic solvent such as benzene, toluene or xylene; or pyridine. The preferred solvent is pyridine.

The ring nitrogen atoms of the formula 1 compounds can be substituted with a $(C_1-C_5)$alkyl group, an alkanoyl group such as an acetyl group, or a benzoyl group. These nitrogen substituted compounds are equivalent to the nitrogen unsubstituted compounds primarily because the substitutent is cleaved upon administration to a patient but also because many of the nitrogen substituted compounds independently possess significant ability to treat or prevent reperfusion injury.

When desired, one or both of the nitrogen atoms of the imidazolecarboxamide ring may be substituted with an alkyl group by any art-known procedure. Such methods include reacting the appropriate N-unsubstituted imidazolecarboxamide of this invention with a base and an alkylating agent in presence of an unreactive solvent. Suitable bases for this reaction can be, for example, a hydride such as sodium hydride or calcium hydride; a phenoxide such as sodium phenoxide; an alkoxide such as sodium ethoxide; or preferably a hydroxide such as sodium hydroxide. Suitable alkylating agents for this reaction are, for example, an alkyl halide such as methyl iodide; or a dialkylsulfate such as dimethylsulfate. Suitable unreactive solvents are, for example, benzene, toluene, or preferably dimethylformamide (DMF). The reaction is allowed to proceed from about 1 minute to about 1 hour and the temperature may be from about 0° C. to about 100° C., preferably about 25° C. When it is desired that only one of the imidazolecarboxamide nitrogen atoms be substituted with an alkyl group, the appropriate imidazolcarboxamide is reacted with from about 1 molar equivalent to about 10 molar equivalents of a base, preferably about 1 molar equivalent and with about 1 molar equivalent of an alkylating agent. Utilizing this procedure, both possible monoalkylated nitrogen isomers result. These isomers are separable by conventional art-known procedures such as fractional crystallization, fractional distillation, or chromatography. When it is desired that both nitrogen atoms of the imidazolecarboxamide ring be alkyl substituted, the appropriate imidazolecarboxamide is reacted with from about 2 molar equivalents to about 10 molar equivalents of a base, preferably about 2 molar equivalents and from about 2 molar equivalents to about 10 molar equivalents of an alkylating agent, preferably about 2 molar equivalents. Finally, any hydroxy substitutents, if present, will become acylated concurrently. That is, when $R_3$ is a phenyl substituted with hydroxy, or when $R_2$ is $NH_2$, such groups are acylated under identical reaction conditions. If desired, the acylation of these substituents may be avoided by the use of suitable protecting groups well-known in the art, for example hydroxy groups may be benzylated and later deblocked by hydrogenolysis.

When desired, the nitrogen atoms of the imidazolecarboxamide ring may be substituted with an alkylcarbonyl or benzoyl group by any suitable art-known procedure. Such methods include reacting the ring N-unsubstituted imidazolecarboxamide of this invention with an acid anhydride. The reactions are allowed to proceed for about 1 to about 20 hours, preferably about 5 hours and the temperature may be from about 0° to about 200° C. preferably from 100° to 150° C. Finally, any hydroxy substituents, if present, will become acylated concurrently. That is, when $R_3$ is a phenyl substituted with hydroxy, or when $R_2$ is $NH_2$, such groups are acylated under identical reaction conditions. If desired, the acylation of these substituents may be avoided by the use of suitable protecting groups well-known in the art, for example hydroxy groups may be benzylated and later deblocked by hydrogenolysis.

The aminoketoamides of formula 2 may be prepared by reduction of the appropriate oxime of formula 3

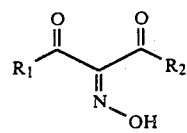

Formula 3 wherein $R_1$ and $R_2$ are as defined above in formula 1. These oximes are reduced by any suitable method generally known in the art such as catalytically in acidic alcoholic medium such as ethanol over an appropriate noble metal catalyst such as palladium on charcoal or with zinc or tin in acetic acid/acetic anhydride solution.

The oximes of formula 3 may be prepared by any suitable art-known procedure such as nitrosation of the appropriate amide of formula 4

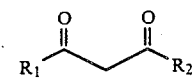

Formula 4 wherein $R_1$ and $R_2$ are as defined above in Formula 1. Suitable nitrosation reactions are reviewed by 0. Tousler in "Organic Reactions," Volume VII, pp. 327–377.

The amount of the active ingredient to be administered can vary widely according to the particular dosage unit employed, the mode of administration, the period of treatment, the age and sex of the patient treated and the nature and extent of the disorder treated. The total amount of the active ingredient to be administered will generally range from about 1 mg/kg to 100 mg/kg and preferably from 3 mg/kg to 30 mg/kg. A unit dosage may contain from 25 to 525 mg of active ingredient, and can be taken one or more times per day. The active compound of formula 1 can be administered with a pharmaceutical carrier using conventional dosage unit forms either orally, parenterally, or topically.

For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, or cornstarch in combination with binders such as acacia, cornstarch, or gelatin, disintegrating agents intented to assist the break-up and dissolution of the tablet following administration such as potato starch, alginic acid, corn starch, or guar gum, lubricants intented to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intented to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane 4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol. A preferred mode of administration is by intraveneous injection or by an intracardiac catheter and will preferably employ an aqueous solution of a compound of structure 1 with sodium hydroxide, preferably about a 12 N solution of sodium hydroxide.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximun number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compounds of formula 1 may be incorporated in the sustained release carrier in a pure form or may be dissolved in any suitable liquid or solid vehicle, including the polymer of which the sustained release carrier is formed.

As used herein the term patient is taken to mean warm blooded animals, for example, birds such as chickens and turkeys, and mammals such as primates including humans, sheep, horses, cattle, pigs, cats, dogs, rats, and mice.

Reperfusion injury is that injury which occurs when molecular oxygen is reintroduced into ischemic tissue. The ischemia can be caused by any means and in any tissue and includes ischemia to the heart or a portion of the heart resulting from a coronary thrombosis or embolism or any other blockage of the blood supply to the heart or a portion of the heart, ischemia surgically induced to the heart of a patient undergoing open-heart or coronary by-pass surgery, the ischemia which occurs to an organ or organ group such as a heart, heart-lung, liver, or kidney to be used in an organ transplant, ischemia occuring during circulatory shock, and ischemia which is caused by blockage of the arteries supplying the brain, i.e. stroke. The compound of structure 1 will ideally be administered to the patient at the time of tissue reperfusion and will continue until such time that reperfusion injury of the type being treated has normally ceased and will be for about 1 to 3 days following substantial reperfusion of the tissue. For example, the compound of structure 1 could conveniently be administered to a patient with a coronary thrombosis concurrently with the administration of a clot dissolving agent such as, tissue plasminogen activator, streptokinase or urokinase. Administration of a compound of structure 1 prior to an ischemia may be indicated in certain instances such as where a patient has substantial risk of heart attack or stroke and would continue until the risk of an ischemic event has substantially disappeared, for example, where the patient has recently suffered a heart attack or stroke, or where the patient is to undergo a surgical procedure requiring a temporary, surgically-induced organ ischemia such as in open heart surgery or coronary by-pass surgery. Use of the compounds of structure 1 to treat reperfusion injury to the heart is the use considered most significant.

The ability of the compound of this invention to reduce reperfusion injury can be demonstrated by its ability to reduce myocardial stunning, i.e. the prolonged loss of contractile function in the absence of necrosis following short periods of myocardial ischemia. (See E. Braunwald and R. A. Kloner, Circ. 66, 1146–1149 (1982). Stunning has been implicated in a variety of disorders and conditions in which blood circulation has been temporarily cut off from the heart or in which a relatively high concentration of oxygen derived free radicals is known to be present.

In order to measure stunning an anesthetized dog is instrumented to record blood pressure, heart rate, electrocardiogram (ECG), cardiac contractile force, and left intraventricular systolic pressure and its derivative. A pair of ultrasonic crystals are implanted one over the other in the area to become ischemic of the left myocardium to measure the thickening of the myocardium between the crystals during contraction. Following a control period, the LAD is occluded for 15 minutes followed by 3 hours of reperfusion. A short period of occlusion is used to prevent any substantial necrosis. During the period of occlusion, the thickening of the myocardial segment between the apical crystals (ischemic myocardium) decreases and actually shows a thinning during contraction in both control and treated dogs. When the occlusion period is ended and reperfusion of the ischemic myocardium has commenced, contractility of the previously ischemic area improves for a short while but does not recover completely and subsequently falls back to the ischemic level within 15 minutes of the reperfusion period. This inability of the contractility (reported as per cent thickening) to recover for anymore than a few minutes during reperfusion is referred to as stunning and is reported below in Table 1 for the test compound 2,3-dihydro—N,N,5-trimethyl-2-thioxo-1H-imidazole-4-carboxamide.

the mixture is stirred at room temperature overnight. The resulting precipitate is recrystallized twice from 50% aqueous ethanol to give the title compound, m.p. 277°–279° C. (dec.).

In a like manner substituting 2-(hydroxyimino)—N-methyl-3-oxobutanamide and N,N-dimethyl-2-(hydroxyimino)-3-oxobutanamide for 2-(hydroxyimino)-N-(4-methoxyphenyl)-3-oxobutanamide in the above procedure results in 2,3-dihydro-N,5-dimethyl-2-thioxo-1H-imidazole-4-carboxamide, m.p. >300° C., and 2,3-dihydro-N,N,5-trimethyl-2-thioxo-1H-imidazole-4-carboxamide, m.p. 243°–245° C., respectively.

EXAMPLE 2

2,3-Dihydro-5-methyl-2-thioxo-1H-imidazole-4-carboxamide

Following the procedure of Example 1 but substituting 2-(hydroxyimino)-3-oxobutanamide for the 2-(hydroxyimino)-N-(4-methoxyphenyl)-3-oxobutanamide gives 2,3-dihydro-5-methyl-2-thioxo-1H-imidazole-4-carboxamide, m.p. <300° C.

EXAMPLE 3

2,3-Dihydro-2-oxo-4,N,N-trimethyl-1H-imidazole-5-carboxamide

A solution of 15.8 g (0.1 mol) of N,N-dimethyl-2-(hydroxyimino)-3-oxobutanamide in 400 ml of ethanol and 100 ml of 2N hydrochloric acid over 2 g of catalyst (5% palladium on charcoal) is hydrogenated in a Paar shaker until 1 molar equivalent of hydrogen is taken up (3–5 hours). The catalyst is removed by filtration. A solution of 16.2 g (0.2 mol) of potassium cyanate in 80 ml of

TABLE 1

PREVENTION OF MYOCARDIAL STUNNING DURING REPERFUSION FOLLOWING 15 MINUTES OF ISCHEMIA IN ANESTHETIZED DOGS
(% Myocardial Thickening ± SE)

| TREATMENT | N | BEFORE LAD OCCLUSION (PRE-)ISCHEMIC AREA | DURING LAD OCCLUSION ISCHEMIC AREA | DURING REPERFUSION at 15 min. ISCHEMIC AREA |
|---|---|---|---|---|
| Control | 4 | 19 ± 4 | −8 ± 3 | −7 ± 3 |
| Test Compound | 4 | 24 ± 2 | −7 ± 2 | 5 ± 2[a] |

[1]Significant difference from percent thickening in the control.

EXAMPLES

The following examples are intended to illustrate this invention and are not intended to limit the scope of this invention in any way.

EXAMPLE 1

2,3-Dihydro-N-(4-methoxyphenyl)-5-methyl-2-thioxo-1H-imidazole-4-carboxamide

To a stirred solution of 11.8 g of 2-(hydroxyimino)—N-(4-methoxyphenyl)-3-oxobutanamide in 30 ml of acetic acid and 10 ml of acetic anhydride at 20–30° C. is added 10 g of zinc dust and the mixture is stirred for 1 hour. Water (150 ml) is added, the mixture is stirred for 2 hours and the zinc is removed by filtration. The filtrate is evaporated to dryness under reduced pressure and the residue is recrystallized from methanol to give 2-acetylamino—N-(4-methoxyphenyl)-3-oxo-butanamide.

This material (10.6 g) is dissolved in 20 ml of 6N hydrochloric acid, the solution is allowed to stand for 5 minutes at room temperature, a solution of 9.7 g of potassium thiocyanate in 80 ml of water is added and water is added, the solution is refluxed for 1 hour and concentrated until the product crystallizes. Recrystallization from 50% aqueous ethanol gives the title compound, m.p. 244°–246° C. (dec).

EXAMPLE 4

2,3-Dihydro-2-oxo-4,N,N-trimethyl-1H-imidazole-5-thiocarboxamide

A suspension of 3.4 g (20 mmol) of 2,3-dihydro—N,N,5-trimethyl-2-oxo-1H-imidazole-4-carboxamide (prepared in example 3) and 4.4 g cf phosphorus pentasulfide in 100 ml of dry pyridine is stirred at reflux temperature for 6 hours. The mixture is allowed to cool overnight and is diluted with water. The precipitate is collected and recrystallized from 50% aqueous ethanol to give the title compound.

EXAMPLE 5

2,3-Dihydro-N,5-dimethyl-2-oxo-1H-imidazole-4-carboxamide

Following the procedure of Example 3 but substituting N,N-dimethyl-2-(hydroxyimino)-3-oxo-butanamide by 2-(hydroxyimino)-N-methyl-3-oxo-butanamide gives 2,3-dihydro-N,5-dimethyl-2-oxo-1H-imidazole-4-carboxamide, m.p. >300° C.

EXAMPLE 6

2,3-Dihydro-5-methyl-2-oxo-1H-imidazole-4-carboxamide

Following the procedure of Example 3 but substituting N,N-dimethyl-2-(hydroxyimino)-3-oxo-butanamide by 2-hydroxyimino)-3-oxobutanamide gives 2,3-dihydro-5-methyl-2-oxo-1H-imidazole-4-carboxamide, m.p. >300° C.

EXAMPLE 7

2,3-dihydro-N-(tert-butyl)-5-methyl-2-oxo-1H-imidazole-4-carboxamide

Following the procedure of Example 3 but substituting N,N-dimethyl-2-(hydroxyimino)-3-oxo-butanamide by N-tert-butyl-2-(hydroxyimino)-3-oxobutanamide gives 2,3-dihydro-5-methyl-N-(tert-butyl)-2-oxo-1H-imidazole-4-carboxamide.

EXAMPLE 8

2,3-Dihydro-5-ethyl—N,N-dimethyl-2-oxo-1H-imidazole-4-carboxamide

Following the procedure of Example 3 but substituting N,N-dimethyl-2-(hydroxyimino)-3-oxobutanamide by N,N-dimethyl-2-(hydroxyimino)-3-oxopentanamide gives 2,3-dihydro- 5-ethyl—N,N-dimethyl-2-oxo-1H-imidazole-4-carboxamide.

EXAMPLE 9

2,3-Dihydro-N-(4-methoxyphenyl)-5-methyl-2-oxo-1H-imidazole-4-carboxamide

To a stirred solution of 11.8 g of 2-(hydroxyimino)—N-(4-methoxyphenyl)-3-oxobutanamide in 30 ml of acetic acid and 10 ml of acetic anhydride at 20 - 30° C. is added 10 g of zinc dust and the mixture is stirred for 1 hour. Water (150 ml) is aded, the mixture is stirred for 2 hours and the zinc is removed by filtration. The filtrate is evaporated to dryness under reduced pressure and the residue is recrystallized from methanol to give 2-acetylamino-N-(4-methoxyphenyl)-3-oxobutanamide.

This material (10.6 g) is dissolved in 20 ml of 6N hydrochloric acid, the solution is allowed to stand for 5 minutes at room temperature, a solution of 9.7 g of potassium cyanate in 80 ml of water is added and the mixture is stirred at room temperature overnight. The resulting precipitate is recrystallized twice from 50% aqueous ethanol to give the title compound, m.p. 299°–301° C. (dec.).

EXAMPLE 10

2,3,-Dihydro-N-(4-methoxyphenyl)-5-methyl-2-thioxo-1H-imidazole--carboxamide

Following the procedure of Example 9 but substituting potassium cyanate by potassium thiocyanate gives 2,3dihydro-N-(4-methoxyphenyl)-5-methyl-2-thioxo-1H-imidazole-4-carboxamide, m.p. 277°–279° C. (dec.)

EXAMPLE 11

Preparation of a Tablet Formulation

Tablets are prepared each having the composition:

| | | Per Tablet |
|---|---|---|
| (a) | 5-Methyl-2-thioxo-1H-imidazole-4-carboxamide | 100 mg |
| (b) | Cornstarch | 15 mg |
| (c) | Lactose | 33.5 mg |
| (d) | Magnesium stearate | 1.5 mg |

EXAMPLE 12

Preparation of a Parenteral Formulation

An injectable unit dosage form is prepared having the composition:

| | | |
|---|---|---|
| (a) | N-(4-pyrridyl)-2-oxo-imidazole-4-carboxamide | 1.000 g |
| (b) | Polyoxyethylene sorbitan monooleate | 2.000 g |
| (c) | Sodium chloride | 0.128 g |
| (d) | Water for injeciton qs ad | 20.000 ml |

We claim:

1. A method of lessening reperfusion injury which comprises administering to a patient suffering from ischemia a therapeutically effective amount of a compound of the structure

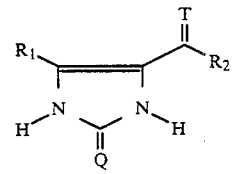

wherein Q and T each independently are a divalent oxygen or sulfur group;

$R_1$ is a hydrogen or a $(C_1-C_4)$ alkyl group; and $R_2$ is a —$NH(R_3)$, or —$N(R_3)(R_4)$ group wherein $R_3$ is a $(C_1-C_4)$alkyl, 2-, 3-, or 4-pyridinyl, 2-, or 3-furanyl, 2-or 3-thienyl, 2- or 3-pyranyl, or a phenyl group optionally substituted at the ortho, meta, or para position with a $(C_1-C_4)$alkyl, $(C_1-C_4)$alkoxy, $(C_1-C_4)$alkylthio, $(C_1-C_4)$alkylsulfone, $(C_1-C_4)$alkylsufoxide, hydroxy, halo, trifluoromethyl, cyano, carboxy, carb$(C_1-C_4)$alkoxy, $(C_1-C_4)$alkylamino, imidazolyl,or methylenedioxy group and wherein $R_4$ is $(C_1-C_4)$alkyl group; or a pharmaceutically acceptable salt thereof.

2. A method of claim 1 wherein T is a divalent oxygen group.

3. A method of one of claims 1 or 2 wherein $R_1$ is a hydrogen or methyl group.

4. A method of one of claims 1 or 2 wherein $R_2$ is a —$NH_2$ group.

5. A method of claim 4 wherein $R_4$ is a hydrogen or methyl group.

6. A method of one of claims 1 or 2 wherein $R_2$ is a —$NHR_3$ group wherein $R_3$ is a $(C_1-C_4)$alkyl group or an optionally substituted phenyl group.

7. A method of claim 6 wherein $R_1$ is a hydrogen or methyl group.

8. A method of one of claims 1 or 2 wherein $R_2$ is a —$NHR_3$ group wherein $R_3$ is a methyl group.

9. A method of claim 8 wherein $R_1$ is a hydrogen or methyl group.

10. A method of one of claims 1 or 2 wherein $R_2$ is a —$NHR_3$ group wherein $R_3$ is a 4-methoxyphenyl group.

11. A method of claim 10 wherein $R_1$ is a hydrogen or methyl group.

12. A method of one of claims 1 or 2 wherein $R_2$ is a —$N(R_3)(R_4)$ wherein $R_3$ and $R_4$ are each a $(C_1-C_4)$alkyl group.

13. A method of claim 12 wherein $R_1$ is a hydrogen or methyl group.

14. A method of one of claims 1 or 2 wherein $R_2$ is a —$N(R_3)(R_4)$ wherein $R_3$ and $R_4$ are each a methyl group.

15. A method of claim 14 wherein $R_1$ is a hydrogen or methyl group.

16. A method of claim 1 wherein T is a divalent oxygen group, $R_1$ is a methyl group, and $R_2$ is a —$N(R_3)(R_4)$ group wherein $R_3$ and $R_4$ are each a methyl group, that is the compound 2,3-dihydro-N,N,5-trimethyl-2-thioxo-1H-imidazole-4-carboxamide.

* * * * *